(12) United States Patent
Morman et al.

(10) Patent No.: US 6,869,424 B1
(45) Date of Patent: Mar. 22, 2005

(54) STRETCHABLE ABSORBENT GARMENT WITH NON-STRETCHABLE LINER

(75) Inventors: Michael Tod Morman, Alpharetta, GA (US); Thomas Walter Odorzynski, Green Bay, WI (US); Georgia Lynn Zehner, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 339 days.

(21) Appl. No.: 09/698,309

(22) Filed: Oct. 27, 2000

(51) Int. Cl.[7] .................................................. A61F 13/15

(52) U.S. Cl. ............. 604/396; 604/385.24; 604/385.29; 604/385.31

(58) Field of Search ................................ 604/396, 367, 604/385.22–385.24, 385.27, 385.29, 385.31

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,036,233 A | 7/1977 | Kozak |
| 4,340,563 A | 7/1982 | Appel et al. |
| 4,543,099 A | 9/1985 | Bunnelle et al. |
| 4,606,964 A | 8/1986 | Wideman |
| 4,640,726 A | 2/1987 | Sallee et al. |
| 4,655,760 A | 4/1987 | Morman et al. |
| 4,663,220 A | 5/1987 | Wisneski et al. |
| 4,687,477 A | 8/1987 | Suzuki et al. |
| 4,699,620 A | 10/1987 | Bernardin |
| 4,699,621 A | 10/1987 | Stevens et al. |
| 4,701,170 A | 10/1987 | Wilson et al. |
| 4,701,171 A * | 10/1987 | Boland et al. ......... 604/385.22 |
| 4,701,172 A | 10/1987 | Stevens |
| 4,701,173 A | 10/1987 | Zehner et al. |
| 4,701,174 A | 10/1987 | Johnson |
| 4,701,175 A | 10/1987 | Boland et al. |
| 4,701,176 A | 10/1987 | Wilson et al. |
| 4,704,114 A | 11/1987 | Wilson et al. |
| 4,704,116 A | 11/1987 | Enloe |

(List continued on next page.)

FOREIGN PATENT DOCUMENTS

| | | |
|---|---|---|
| EP | 0 214 636 | 11/1991 |
| EP | 0 236 032 | 12/1991 |
| EP | 0 217 032 | 2/1992 |
| EP | 0 386 816 | 4/1994 |
| EP | 0 320 991 | 5/1994 |
| EP | 0 412 579 | 6/1994 |
| EP | 0 400 111 | 8/1994 |

(List continued on next page.)

Primary Examiner—Jacqueline Stephens
(74) Attorney, Agent, or Firm—Pauley Petersen & Erickson

(57) ABSTRACT

A form-fitting, pant-like, absorbent garment that does not result in bagging and wrinkling of the bodyside liner. The garment has a stretchable outer cover and a non-stretchable bodyside liner with a free-floating absorbent assembly located between the stretchable outer cover and the non-stretchable bodyside liner. A pair of highly stretchable side panels and/or at least one highly stretchable waist member are attached to the non-stretchable bodyside liner. The total transverse stretchability of the side panels is roughly equal to the transverse stretchability of the outer cover, thereby enabling the outer cover to stretch freely without inhibiting the non-stretchable bodyside liner. Alternatively, or additionally, the total longitudinal stretchability of the waist members is roughly equal to the longitudinal stretchability of the outer cover, thereby also enabling the outer cover to stretch freely without inhibiting the non-stretchable bodyside liner.

40 Claims, 9 Drawing Sheets

U.S. PATENT DOCUMENTS

| | | |
|---|---|---|
| 4,718,900 A | 1/1988 | Boland et al. |
| 4,720,415 A | 1/1988 | Vander Wielen et al. |
| 4,747,846 A | 5/1988 | Boland et al. |
| 4,756,709 A | 7/1988 | Stevens |
| 4,770,656 A | 9/1988 | Proxmire et al. |
| 4,801,485 A | 1/1989 | Sallee et al. |
| 4,808,176 A | 2/1989 | Kielpikowski |
| 4,834,736 A * | 5/1989 | Boland et al. ......... 604/385.22 |
| 4,834,738 A | 5/1989 | Kielpikowski et al. |
| 4,834,742 A | 5/1989 | Wilson et al. |
| 4,838,885 A | 6/1989 | Bernardin |
| 4,842,596 A | 6/1989 | Kielpikowski et al. |
| 4,846,825 A | 7/1989 | Enloe et al. |
| 4,863,779 A | 9/1989 | Daponte |
| 4,872,871 A | 10/1989 | Proxmire et al. |
| 4,892,598 A * | 1/1990 | Stevens et al. ............... 156/91 |
| 4,908,247 A | 3/1990 | Baird et al. |
| 4,940,464 A | 7/1990 | Van Gompel et al. |
| 4,965,122 A | 10/1990 | Morman |
| 4,981,747 A | 1/1991 | Morman |
| 5,037,416 A * | 8/1991 | Allen et al. ............ 604/385.22 |
| 5,046,272 A | 9/1991 | Vogt et al. |
| 5,104,116 A | 4/1992 | Pohjola |
| 5,114,781 A | 5/1992 | Morman |
| 5,116,662 A | 5/1992 | Morman |
| 5,143,679 A | 9/1992 | Weber et al. |
| 5,156,793 A | 10/1992 | Buell et al. |
| 5,167,897 A | 12/1992 | Weber et al. |
| 5,171,388 A | 12/1992 | Hoffman et al. |
| 5,224,405 A | 7/1993 | Pohjola |
| 5,226,992 A | 7/1993 | Morman |
| 5,244,482 A | 9/1993 | Hassenboehler, Jr. et al. |
| 5,246,433 A * | 9/1993 | Hasse et al. ................ 604/396 |
| 5,259,902 A | 11/1993 | Muckenfuhs |
| 5,336,545 A | 8/1994 | Morman |
| 5,354,400 A | 10/1994 | Lavash et al. |
| 5,385,775 A | 1/1995 | Wright |
| 5,397,316 A | 3/1995 | LaVon et al. |
| 5,492,753 A | 2/1996 | Levy et al. |
| 5,496,429 A | 3/1996 | Hasse et al. |
| 5,514,470 A | 5/1996 | Haffner et al. |
| 5,527,302 A | 6/1996 | Endres et al. |
| 5,554,143 A | 9/1996 | Roe et al. |
| 5,554,144 A | 9/1996 | Roe et al. |
| 5,554,145 A | 9/1996 | Roe et al. |
| 5,556,394 A | 9/1996 | Roe et al. |
| 5,556,504 A | 9/1996 | Rajala et al. |
| 5,560,878 A | 10/1996 | Dragoo et al. |
| 5,562,648 A | 10/1996 | Peterson |
| 5,569,232 A | 10/1996 | Roe et al. |
| 5,569,234 A * | 10/1996 | Buell et al. ................ 604/396 |
| 5,582,903 A | 12/1996 | Levy et al. |
| 5,587,225 A | 12/1996 | Griesbach et al. |
| 5,591,155 A * | 1/1997 | Nishikawa et al. ......... 604/393 |
| 5,593,400 A | 1/1997 | O'Leary |
| 5,611,790 A | 3/1997 | Osborn, III et al. |
| 5,615,460 A | 4/1997 | Weirich et al. |
| 5,624,422 A | 4/1997 | Allen |
| 5,624,427 A | 4/1997 | Bergman et al. |
| 5,624,729 A | 4/1997 | Cohen et al. |
| 5,628,741 A | 5/1997 | Buell et al. |
| 5,628,856 A | 5/1997 | Dobrin et al. |
| 5,635,290 A | 6/1997 | Stopper et al. |
| 5,643,242 A | 7/1997 | Lavon et al. |
| 5,643,396 A | 7/1997 | Rajala et al. |
| 5,645,672 A | 7/1997 | Dobrin |
| 5,658,269 A | 8/1997 | Osborn, III et al. |
| 5,660,657 A | 8/1997 | Rajala et al. |
| 5,674,212 A | 10/1997 | Osborn, III et al. |
| 5,683,375 A | 11/1997 | Osborn, III et al. |
| 5,685,874 A * | 11/1997 | Buell et al. ................. 604/396 |
| 5,690,627 A | 11/1997 | Clear et al. |
| 5,702,382 A | 12/1997 | Osborn, III et al. |
| 5,713,884 A | 2/1998 | Osborn, III et al. |
| 5,716,478 A | 2/1998 | Boothe et al. |
| 5,749,866 A | 5/1998 | Roe et al. |
| 5,749,989 A | 5/1998 | Linman et al. |
| 5,759,340 A | 6/1998 | Boothe et al. |
| 5,843,056 A * | 12/1998 | Good et al. ................ 604/367 |
| 5,843,068 A * | 12/1998 | Allen et al. ............ 604/385.22 |
| 5,853,405 A | 12/1998 | Suprise |
| 5,883,028 A | 3/1999 | Morman et al. |
| 5,899,896 A | 5/1999 | Suprise et al. |
| 5,910,224 A | 6/1999 | Morman |
| 5,931,827 A * | 8/1999 | Buell et al. ............ 604/385.29 |
| 6,004,306 A | 12/1999 | Robles et al. |
| 6,020,535 A | 2/2000 | Blenke et al. |

FOREIGN PATENT DOCUMENTS

| | | | |
|---|---|---|---|
| EP | 0 451 705 | 8/1994 | |
| EP | 0 630 630 | 12/1994 | |
| EP | 0 630 631 | 12/1994 | |
| EP | 0 630 632 | 12/1994 | |
| EP | 0 420 256 | 5/1995 | |
| EP | 0 707 106 | 4/1996 | |
| EP | 0 433 951 | 8/1996 | |
| EP | 0 552 345 | 9/1996 | |
| EP | 0 613 360 | 9/1996 | |
| EP | 0 630 221 | 4/1997 | |
| EP | 0 409 315 | 5/1997 | |
| EP | 0 820 747 | 1/1998 | |
| EP | 0 602 613 | 6/1998 | |
| EP | 0 651 629 | 6/1998 | |
| EP | 0 659 117 | 6/1998 | |
| WO | 93/01785 | 2/1993 | |
| WO | 93/17648 | 9/1993 | |
| WO | 94/02094 | 2/1994 | |
| WO | 96/03953 | 2/1996 | |
| WO | 96/16625 | 6/1996 | |
| WO | 96/18367 | 6/1996 | |
| WO | 97/36566 | 10/1997 | |
| WO | 99/33425 | 7/1999 | |
| WO | WO 99/60966 | * 12/1999 | ........... A61F/13/15 |
| WO | 99/60967 | 12/1999 | |
| WO | 99/60968 | 12/1999 | |
| WO | 99/60972 | 12/1999 | |
| WO | 99/60974 | 12/1999 | |

* cited by examiner

STRETCHABLE ABSORBENT GARMENT WITH NON-STRETCHABLE LINER

FIELD OF THE INVENTION

This invention is directed to personal care absorbent products having a stretchable outer cover and a non-stretchable bodyside liner.

BACKGROUND OF THE INVENTION

Pant-like absorbent garments, such as adult incontinence products, infant and children's diapers, swim wear and training pants, typically have some degree of stretchability in order to conform to a wearer's body. Present diapers, for example, have stretchable side panels with non-stretchable outer covers, bodyside liners and absorbent assemblies. When this type of diaper is worn, only the side panels stretch.

To make a totally stretchable, form-fitting pant-like absorbent garment, it is necessary to have a stretchable outer cover. Totally stretchable diapers have proven to be successful in terms of providing a form-fitting product. However, in order to function properly, the bodyside liner and/or absorbent assembly, which operate in parallel with the outer cover, must also stretch. Designs which have the absorbent assembly "free floating" allow the outer cover and bodyside liner to stretch independently of the absorbent assembly, thereby removing the requirement for a stretchable absorbent assembly. The requirement of a stretchable bodyside liner remains a problem. Reversibly necked spunbond material is known from U.S. Pat. No. 4,965,122, issued to Morman. This material has the needed elongation for a stretchable bodyside liner, but has minimal retractive force and, thus, does not prevent bagging and wrinkling of the bodyside liner.

There is a need or desire for stretchable, form-fitting, pant-like, personal care absorbent garments that minimize or eliminate bagging and wrinkling of the bodyside liner.

SUMMARY OF THE INVENTION

The present invention is directed to pant-like absorbent garments having a stretchable outer cover and a non-stretchable bodyside liner. The stretchable outer cover can stretch in a transverse, or cross direction, or the outer cover can stretch in a longitudinal, or machine direction, or the outer cover can stretch in both a transverse direction and a longitudinal direction.

In one embodiment of the invention, the non-stretchable bodyside liner is attached to a pair of highly stretchable side panels. The total elongation of the side panels in centimeters in the transverse direction is roughly equal to the elongation of the outer cover in centimeters in the transverse direction. More particularly, the side panels have a percentage transverse stretch equal to at least one-half of a percentage transverse stretch of the outer cover times a width of the outer cover divided by a total width of the side panels. This design allows for the outer cover to freely stretch in the transverse direction while using a non-stretchable bodyside liner. In another embodiment of the invention, the non-stretchable bodyside liner is attached to a highly stretchable front waist member and/or a highly stretchable back waist member. The total elongation of the front and/or back waist members in centimeters in the longitudinal direction is roughly equal to the elongation of the outer cover in centimeters in the longitudinal direction. More particularly, the waist members have a percentage longitudinal stretch equal to at least one-half of a percentage longitudinal stretch of the outer cover times a length of the outer cover divided by a total length in the longitudinal direction of the waist members. This design allows for the outer cover to freely stretch in the longitudinal direction while using a non-stretchable bodyside liner.

In yet another embodiment of the invention, the non-stretchable bodyside liner is attached to a pair of highly stretchable side panels and to a highly stretchable front waist member and/or a highly stretchable back waist member. The total elongation of the side panels in centimeters in the transverse direction is roughly equal to the elongation of the outer cover in centimeters in the transverse direction. Similarly, the total elongation of the waist members in centimeters in the longitudinal direction is roughly equal to the elongation of the outer cover in centimeters in the longitudinal direction. More particularly, the side panels have a percentage transverse stretch equal to at least one-half of a percentage transverse stretch of the outer cover times a width of the outer cover divided by a total width of the side panels, and the waist members have a percentage longitudinal stretch equal to at least one-half of a percentage longitudinal stretch of the outer cover times a length of the outer cover divided by a total length of the waist members in the longitudinal direction. This design allows for the outer cover to freely stretch in both the transverse and longitudinal directions while using a non-stretchable bodyside liner.

A non-stretchable absorbent assembly can be attached to the non-stretchable bodyside liner between the bodyside liner and the stretchable outer cover, or can be free floating between the bodyside liner and the outer cover. As described, the outer cover can stretch to conform to the wearer's body without requiring any stretch from the bodyside liner, and therefore without requiring any stretch from the absorbent assembly. Consequently, the capillary structure of the absorbent assembly and the bodyside liner is not changed by the stretching of the resulting garment. Thus, constant porosity can be maintained within the absorbent assembly and the bodyside liner regardless of the level of stretching of the outer cover.

With the foregoing in mind, it is a feature and advantage of the invention to provide a form-fitting, pant-like, absorbent garment that minimizes or eliminates bagging and wrinkling of the bodyside liner.

It is another feature and advantage of the invention to provide a material assembly that can maintain constant porosity while being stretched.

DEFINITIONS

Figure 1:
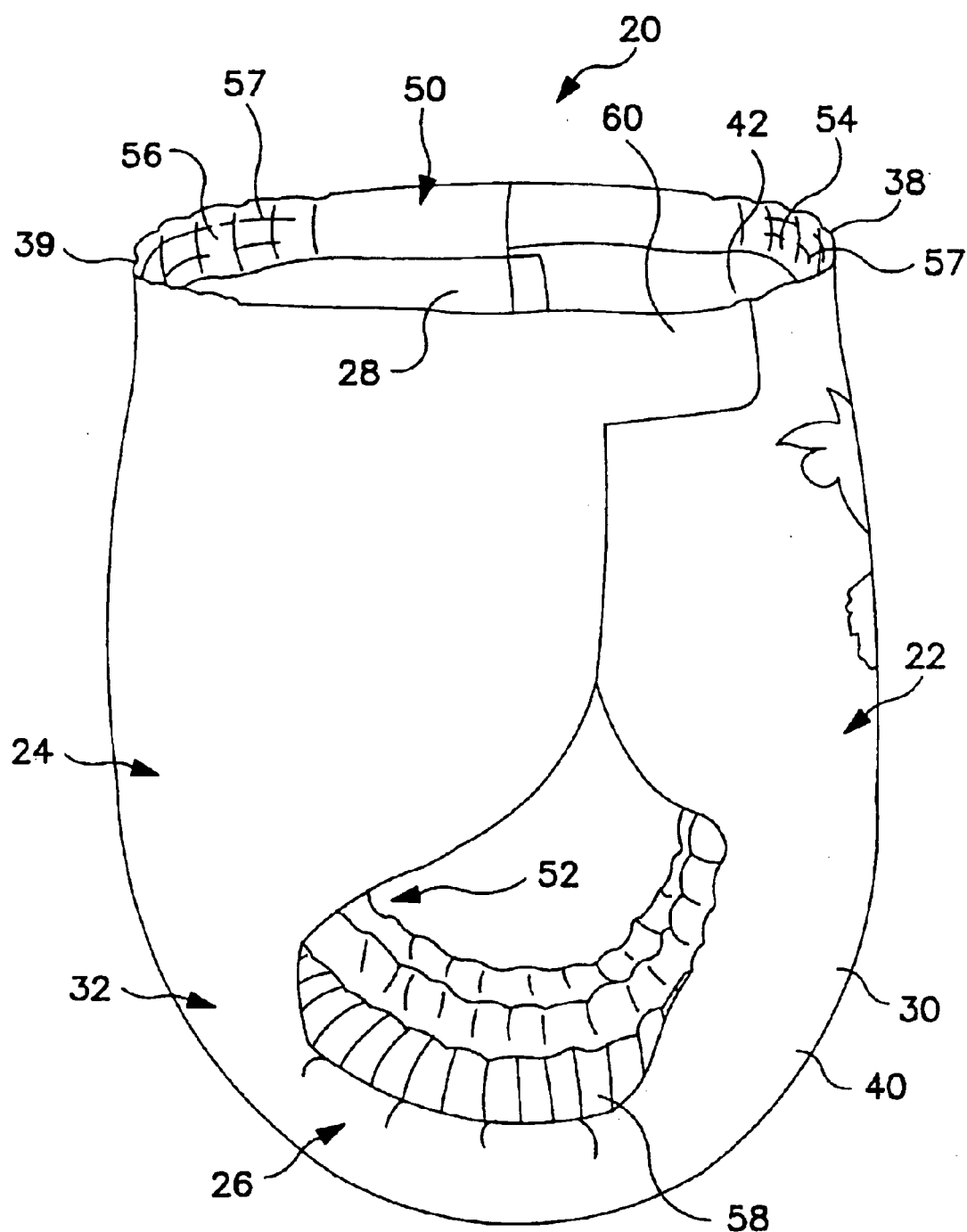
FIG. 1 is a side perspective view of an absorbent garment having a stretchable outer cover and a non-stretchable bodyside liner, in a fastened position.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 40 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Integral" or "integrally" is used to refer to various portions of a single unitary element rather than separate structures bonded to or placed with or placed near one another.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 2:
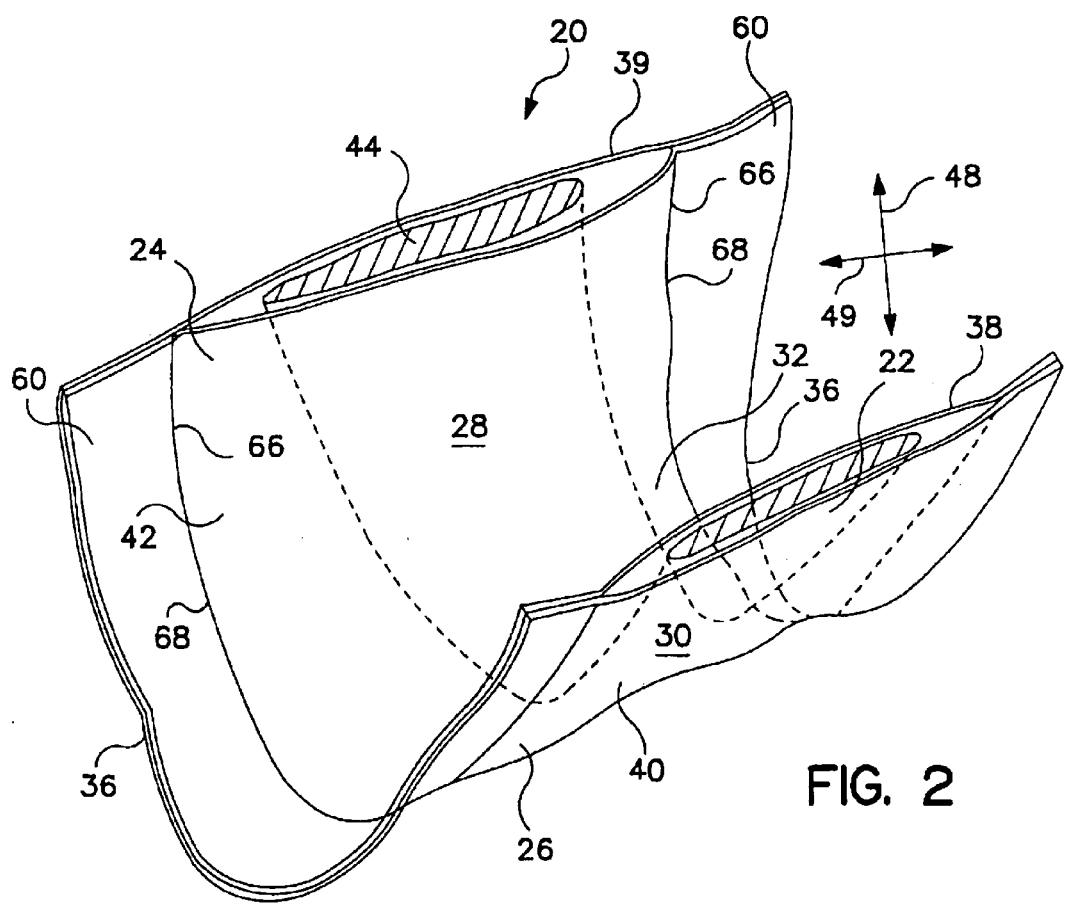
FIG. 2 is a plan view of one embodiment of an absorbent garment having a stretchable outer cover and a non-stretchable bodyside liner, in an unfastened position.
Figure 3:
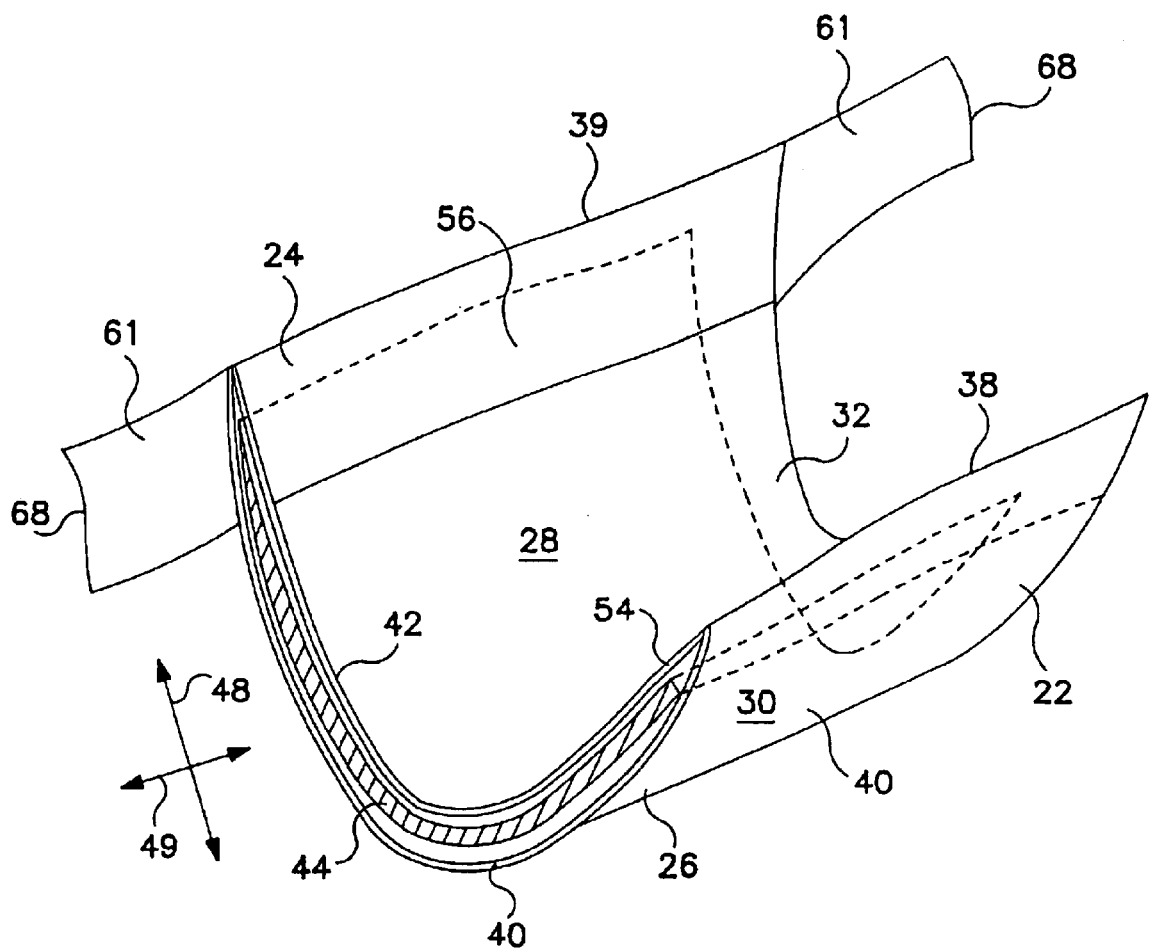
FIG. 3 is a plan view of another embodiment of an absorbent garment having a stretchable outer cover and a non-stretchable bodyside liner, in an unfastened position.
Figure 4:
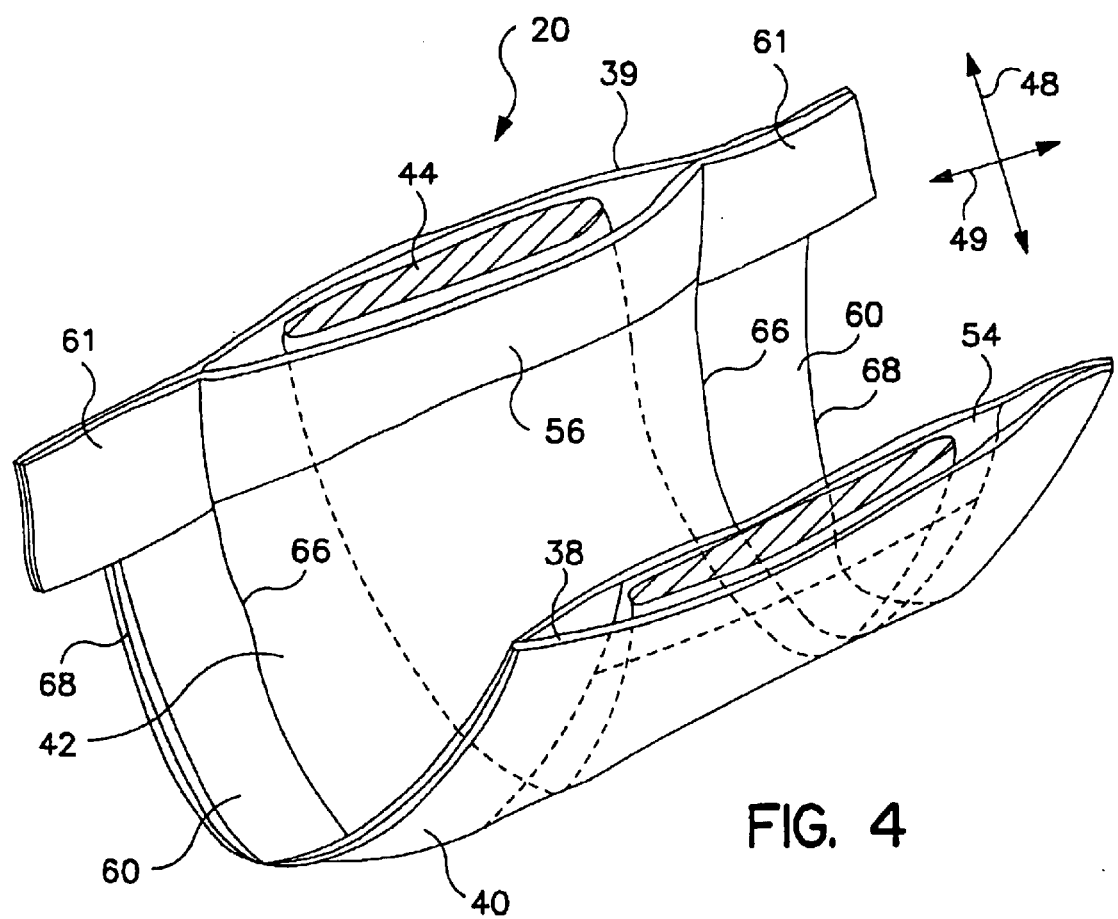
FIG. 4 is a plan view of yet another embodiment of an absorbent garment having a stretchable outer cover and a non-stretchable bodyside liner, in an unfastened position.

"Longitudinal" and "transverse" have their customary meaning, as indicated by the longitudinal and transverse axes depicted in FIGS. 2–4. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Non-stretchable" means that a material can only be stretched, without breaking, by less than 50% in at least one direction, in other words, to less than 150% of its initial (unstretched) length in at least one direction, suitably less than 30%, or less than 130% of its initial length, desirably less than 10%, or less than 110% of its initial length.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Polymers" include, but are not limited to, homopolymers, copolymers, such as for example, block, graft, random and alternating copolymers, terpolymers, etc. and blends and modifications thereof Furthermore, unless otherwise specifically limited, the term "polymer" shall include all possible geometrical configurations of the material. These configurations include, but are not limited to isotactic, syndiotactic and atactic symmetries.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. No. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, by at least 50% to at least 150% of its initial (unstretched) length in at least one direction, suitably by at least 100% to at least 200% of its initial length, desirably by at least 150% to at least 250% of its initial length. The term includes elastic materials as well as materials that stretch but do not significantly retract.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to a form-fitting, stretchable, pant-like, absorbent garment having a stretchable outer cover and a non-stretchable bodyside liner.

The principles of the present invention can be incorporated into any suitable disposable, pant-like, absorbent article. Examples of such suitable articles include diapers, training pants, incontinence products, swim wear, other personal care or health care garments, or the like. For ease of explanation, the description hereafter will be in terms of a diaper.

Referring to FIGS. 1 and 2, a disposable absorbent article, such as a diaper 20, is illustrated. The diaper 20 includes an absorbent chassis 32. The absorbent chassis 32 defines a front region 22, a back region 24, a crotch region 26 interconnecting the front and back regions, an inner surface 28 which is configured to contact the wearer, and an outer surface 30 opposite the inner surface which is configured to contact the wearer's clothing. With additional reference to FIG. 2, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39.

For reference, arrows 48 and 49 depicting the orientation of the longitudinal axis and the transverse axis, respectively, of the diaper 20 are illustrated in FIGS. 2, 3 and 4.

In one embodiment of the invention, shown in FIG. 2, the diaper 20 includes a stretchable outer cover 40, a non-stretchable bodyside liner 42 which is connected to the outer cover in a superposed relation, a free-floating absorbent assembly 44 which is located between the outer cover 40 and the bodyside liner 42, and a pair of highly stretchable side panels 60 or side tabs attached to the outer cover 40 along a distal edge 68 and attached to the bodyside liner 42 along attachment line 66. These highly stretchable side panels 60 can stretch and retract at least in the transverse, or cross machine direction 49. The highly stretchable side panels 60 can be tabs, straps, tearable seams, or similar devices, that can be fastened between the front region 22 and the back region 24 by suitable means, including adhesives. The outer cover 40 is stretchable and retractable at least in the transverse direction 49.

As shown in the diaper 20 in FIG. 1, the front and back regions 22 and 24 together define a three-dimensional pant configuration having a waist opening 50 and a pair of leg openings 52. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52. The front region 22 includes the portion of the diaper 20 which, when worn, is positioned on the front of the wearer while the back region 24 includes the portion of the diaper which, when worm, is positioned on the back of the wearer. The crotch region 26 of the diaper 20 includes the portion of the diaper which, when worn, is positioned between the legs of the wearer and covers the lower torso of the wearer. The highly stretchable side panels 60 of the diaper 20, when worm are positioned forward from the hips of the wearer.

The absorbent chassis 32 is configured to contain and/or absorb any kit body exudates discharged from the wearer. For example, the absorbent chassis 32 can include a pair of elasticized containment flaps (not shown) which are configured to provide a barrier to the transverse flow of body exudates. The elasticized containment flaps define an unattached edge which assumes an upright, generally perpendicular configuration in at least the crotch region 26 of the training pant 20 to form a seal against the wearer's body. Suitable constructions and arrangements for the containment flaps are generally well known to those skilled in the art and are described in U.S. Pat. No. 4,704,116 issued Nov. 3, 1987 to Enloe, which is incorporated herein by reference.

In another embodiment of the present invention, shown in FIG. 3, the diaper 20 includes a stretchable outer cover 40, a non-stretchable bodyside liner 42 which is connected to the outer cover in a superposed relation, a free-floating absorbent assembly 44 which is located between the outer cover 40 and the bodyside liner 42, a highly stretchable front waist member 54 attached to the outer cover along the front waist edge 38 and attached to the bodyside liner inward from the front waist edge 38, a highly stretchable back waist member 56 attached to the outer cover along the back waist edge 39 and attached to the bodyside liner inward from the back waist edge 39, and a pair of side panels 60 or side tabs attached to the outer cover 40 and/or the highly stretchable back waist member 56. The highly stretchable front and back waist members 54 and 56 can stretch and retract at least in the longitudinal, or machine direction 48. Similarly, in this embodiment, the stretchable outer cover 40 is stretchable and retractable at least in the longitudinal direction 48.

In yet another embodiment of the present invention, shown in FIG. 4, the diaper 20 includes a stretchable outer cover 40, a non-stretchable bodyside liner 42 which is connected to the outer cover in a superposed relation, a free-floating absorbent assembly 44 which is located between the outer cover 40 and the bodyside liner 42, a highly stretchable front waist member 54 attached to the outer cover along the front waist edge 38 and attached to the bodyside liner inward from the front waist edge 38, a highly stretchable back waist member 56 attached to the outer cover along the back waist edge 39 and attached to the bodyside liner inward from the back waist edge 39, a pair of highly stretchable side panels 60 attached to the outer cover 40 along a distal edge 68 and attached to the bodyside liner 42 and/or to the highly stretchable back waist member 56 along attachment line 66, and a pair of side tabs 61 attached to the back waist member 56 and/or the side panels 60. The highly stretchable front and back waist members 54 and 56 can stretch and retract at least in the longitudinal direction 48. The highly stretchable side panels 60 can stretch and retract at least in the transverse direction 49. The highly stretchable side panels 60 can be tabs, straps, tearable seams, or similar devices, that can be fastened to the front portion 22 of the outer cover 40 by suitable means, including adhesives. The outer cover 40 in this embodiment is stretchable and retractable in both the longitudinal direction 48 and the transverse direction 49.

The stretchable outer cover 40, due to its stretchability and retractability in the transverse direction 49, forms a physical seal between the wearer and the absorbent garment 20 at the front waist edge 38 and the back waist edge 39 of the absorbent garment, even when no waist members 54 or 56 are included in the diaper 20. To further enhance containment and/or absorption of body exudates, the diaper 20 can include waist elastic members 57 and/or leg elastic members 58, as are known to those skilled in the art (FIG. 1). The waist elastic members 57 can be operatively joined to the stretchable outer cover 40 and/or the non-stretchable bodyside liner 42 and/or the highly stretchable waist members 54 and 56, parallel to the opposite waist edges 38 and 39, and can extend over part or all of the waist edges. The leg elastic members 58 are desirably operatively joined to the stretchable outer cover 40 and/or the non-stretchable bodyside liner 42 longitudinally along the opposite side edges 36 and positioned in the crotch region 26 of the diaper 20.

The waist elastic members 57 and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E.I. DuPont de Nemours and Company, Wilmington, Del., U.S.A.

The stretchable outer cover 40 can suitably be stretched in the longitudinal direction and/or the transverse direction by about 25% to about 300%, to between about 125% and about 400% of an unstretched length and/or width of the outer cover. More suitably, the stretchable outer cover 40 can be stretched by about 40% to about 250%, to between about 140% and about 350% of the unstretched length and/or width of the outer cover. Even more suitably, the stretchable outer cover 40 can be stretched by about 50% to about 200%, to between about 150% and about 300% of the unstretched length and/or width of the outer cover.

The stretchable outer cover 40 desirably includes a material that is substantially liquid impermeable. The stretchable outer cover 40 can be a single layer of liquid impermeable material, but desirably includes a multi-layered laminate 20 structure in which at least one of the layers is liquid impermeable. For instance, the stretchable outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A.

The liquid permeable outer layer can be any suitable material and desirably one that provides a generally cloth-like texture. One example of such a material is a thermoplastic nonwoven web, such as a spunbond thermoplastic nonwoven web made from a stretchable polymer and having a basis weight of about 1–100 grams per square meter (gsm), suitably about 5–50 gsm, more suitably 10–30 gsm. Suitable stretchable polymers for making the nonwoven web include certain flexible polyolefins, for example propylene-based polymers having both atactic and isotactic propylene groups in the main polypropylene chain. Flexible polyolefins (FPO's) are sold by the Rexene Corporation. Also included are heterophasic propylene-ethylene copolymers sold as "catalloys" by the Himont Corporation. Heterophasic polymers are reactor blends formed by adding different levels of propylene and ethylene at different stages in the reactor. Heterophasic polymers typically include about 10–90% by weight of a first polymer segment A, about 10–90% by weight of a second polymer segment B, and 0–20% by weight of a third polymer segment C. Polymer segment A is at least about 80% crystalline and includes about 90–100% by weight propylene, as a homopolymer or random copolymer with up to 10% by weight ethylene. Polymer segment B is less than about 50% crystalline, and includes about 30–70% by weight propylene randomly copolymerized with about 30–70% by weight ethylene. Optional polymer segment C contains about 80–100% by weight ethylene and 0–20% of randomly copolymerized propylene.

Other stretchable polymers include very low density polyethylene (VLDPE), which is an ethylene-alpha olefin copolymer having a density less than 0.900 grams/cm$^3$, preferably about 0.870–0.890 grams/cm$^3$. Preferred VLDPE's are single-site catalyzed. Other extendible polymers include random propylene-alpha olefin copolymers containing more than 10% by weight of a $C_2$ or $C_4$-$C_{12}$ comonomer, preferably about 15–85% by weight of the comonomer, with ethylene being a preferred comonomer.

The inner layer of the stretchable outer cover 40 can be both liquid and vapor impermeable, or can be liquid impermeable and vapor permeable. The inner layer is desirably manufactured from a thin (1–50 microns, suitably 5–25 microns, more suitably 10–20 microns) plastic film, although other stretchable liquid impermeable materials may also be used. The film can contain a blend of a thermoplastic polymer and a 30–70% by weight of a particulate inorganic filler, such as calcium carbonate. The film can be oriented at least uniaxially to cause void formation around the filler particles, resulting in breathability. Suitable stretchable polymers for making the film include stretchable olefin polymers, such as an olefinic copolymer of polyethylene. More specifically, other stretchable polymers include diblock, triblock, tetrablock or other multi-block elastomeric copolymers such as olefinic copolymers, including styrene-isoprene-styrene, styrene-butadiene-styrene, styrene-ethylene/butylene-styrene, or styrene-ethylene/propylene-styrene, which may be obtained from the Shell Chemical Company, under the trade designation KRATON® elastomeric resin; polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; and single-site or metallocene-catalyzed polyolefins having density less than about 0.89 grams/cc, available from Dow Chemical Co. under the trade name AFFINITY®. The inner layer, or the liquid impermeable stretchable outer cover 40 when a single layer, prevents waste material from wetting articles, such as bedsheets and clothing, as well as the wearer and care giver.

Suitable materials for the stretchable outer cover 40 include a spunbonded laminate, a meltblown laminate, a spunbond-meltblown-spunbond laminate, a neck-bonded laminate (NBL), or a stretch-bonded laminate (SBL) made using a stretchable polymer or blend thereof A more specific example of a suitable liquid impermeable film for use as a liquid impermeable inner layer, or a single layer liquid impermeable stretchable outer cover 40, is a 0.2 millimeter polyethylene film commercially available from Huntsman Packaging of Newport News, Va., U.S.A. If the stretchable outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the stretchable outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Another example of a suitable material for the stretchable outer cover is a breathable elastic film/nonwoven laminate, described in U.S. Pat. No. 5,883,028, issued to Morman et al., herein incorporated by reference. The outer cover can be one-way extendable, one-way stretchable and retractable, two-way extendable, or two-way stretchable and retractable. Examples of materials having one-way stretchability and retractability are disclosed in U.S. Pat. No. 4,720,415 issued to Vander Wielen, et al., U.S. Pat. No. 5,336,545 issued to Morman, U.S. Pat. No. 4,981,747 issued to Morman, U.S. Pat. No. 5,226,992 issued to Morman, and U.S. Pat. No. 5,910,224 issued to Morman, all of which are hereby incorporated by reference. Examples of materials having two-way stretchability and retractability are disclosed in U.S. Pat. No. 5,116,662 issued to Morman and U.S. Pat. No. 5,114,781 issued to Morman, both of which are hereby incorporated by reference.

The liquid permeable, non-stretchable bodyside liner 42 is illustrated as overlying the stretchable outer cover 40 and absorbent assembly 44, and may but need not have the same dimensions as the stretchable outer cover 40. The non-stretchable bodyside liner 42 is desirably compliant, soft feeling, and non-irritating to the child's skin. Further, the non-stretchable bodyside liner 42 can be less hydrophilic than the absorbent assembly 44, to present a relatively dry surface to the wearer and permit liquid to readily penetrate through its thickness.

The non-stretchable bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the non-stretchable bodyside liner 42. For example, the non-stretchable bodyside liner 42 can be composed of a melt-blown or spunbonded web of polyolefin fibers. The non-stretchable bodyside liner 42 can also be a bonded-carded web composed of natural and/or synthetic fibers. The non-stretchable bodyside liner 42 can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVELO® N-62 from Hodgson Textile Chemicals of Mount Holly, N.C., U.S.A. and GLUCOPONO® 220UP from Henkel Corporation of Ambler, Pa., in an active ratio of 3:1. The surfactant can be applied by any conventional means, such as spraying, printing, brush coating or the like. The surfactant can be applied to the entire non-stretchable bodyside liner 42 or can be selectively applied to particular sections of the non-stretchable bodyside liner, such as the medial section along the longitudinal centerline.

A suitable liquid permeable, non-stretchable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. In general, polyethylene polymers and copolymers having a density of 0.900 grams/cc or greater tend to be less extendible or not extendible, while those having a density below 0.900 grams/cc are more extendible. As mentioned, in general, polypropylene polymers and copolymers containing 0–10% of an ethylene or other alpha-olefin comonomer tend to be less extendible or not extendible, while propylene-alpha olefin copolymers containing more than 10% comonomer are more extendible. Non-extendible materials are preferred for the bodyside liner 42.

The absorbent assembly 44 (FIGS. 2–4) is positioned between the stretchable outer cover 40 and the non-stretchable bodyside liner 42, which components can be joined together by any suitable means, such as adhesives, as is well known in the art. The absorbent assembly 44 is desirably "free-floating" between the stretchable outer cover 40 and the non-stretchable bodyside liner 42. As used herein, the term "free-floating" refers to two or more components having little or no bonding between them. As shown in FIGS. 11–14, the free-floating absorbent assembly 44 has one bond point 74 between the absorbent assembly 44 and the stretchable outer cover 40. Because the absorbent assembly 44 is free-floating, the absorbent assembly 44 can be non-stretchable.

Capillary structure, or porosity, of a material changes as the material is stretched. The capillary structure, or porosity, is an important factor that influences liquid absorption. As described, the outer cover 40 can stretch to conform to the wearer's body without requiring any stretch from the bodyside liner 42, and therefore without requiring any stretch from the absorbent assembly 44. Consequently, the capillary structure of the absorbent assembly 44, as well as the capillary structure of the bodyside liner 42, is not changed by the stretching of the diaper 20. Thus, constant porosity can be maintained within the absorbent assembly 44 and the bodyside liner 42 regardless of the level of stretching of the outer cover 40. The capillary structure of the absorbent assembly 44 and the bodyside liner 42 can therefore be optimized and constant porosity can be maintained at any level of stretching of the outer cover 40.

The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from so about 5 to about 90 weight percent based on total weight of the absorbent assembly. The absorbent assembly 44 suitably has a density within the range of about 0.10 to about 0.50 grams per cubic centimeter. The absorbent assembly 44 may or may not be wrapped or encompassed by a suitable tissue wrap that maintains the integrity and/or shape of the absorbent assembly.

The absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the illustrated diaper 20 in FIGS. 2 and 4 has a pair of highly stretchable side panels 60 with one side panel disposed on either side of the absorbent t chassis 32. The transversely opposed side panels 60 can b e permanently bonded to the absorbent chassis 32 in the back region 24. More particularly, as shown best in FIG. 2, the side panels 60 can be permanently bonded to the outer cover 40 along the distal edge 68 and to the bodyside liner 42 along the attachment line 66. By attaching the side panels 60 in this manner, the side panels 60 are each anchored to the non-stretchable bodyside liner 42 at one end, yet the side panels 60 can stretch in the transverse direction 49 when the outer cover 40 is stretched in the transverse direction. The side panels 60 may be attached using attachment means known to those skilled in the a art such as adhesive, thermal or ultrasonic bonding.

In particular embodiments for improved fit and appearance, the side panels 60 of the diaper 20 can have an average length dimension measured parallel to the longitudinal axis 48 that ranges anywhere between about 3 percent and about 100 percent of the overall length dimension of the absorbent article, also measured parallel to the longitudinal axis 48. For example, in diapers having an overall length dimension of about 40 centimeters, the side panels 60 desirably have an average length dimension between a bout 1.2 centimeters and about 40 centimeters.

Each of the side panels 60 can include one or more individual, distinct pieces of material. The side panels 60 include an elastic material capable of stretching in a direction generally parallel to the transverse axis 49 of the diaper 20. Desirably, each side panel 60 is also capable of stretching in a direction generally parallel to the longitudinal axis 48.

Suitable elastic materials, as well as on e described process of incorporating elastic side panels into an absorbent garment, are described in the following U.S. Patent: U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL) a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the stretchable outer cover 40. Suitable elastic polymers for making the side panels 60 include the same polymers that can be used to make the stretchable outer cover 40. Other suitable elastic polymers include, without limitation, elastomeric (single-site or metallocene catalyzed) polypropylene, polyethylene and other alpha-olefin homopolymers and copolymers, having density less than about 0.89 grams/cc; ethylene vinyl acetate copolymers; and substantially amorphous copolymers and terpolymers of ethylene-propylene, butene-propylene, and ethylene-propylene-butene.

The side panels 60 are highly stretchable and can be stretched by about 75% to about 1400% in the transverse direction, to between about 175% and about 1500% of an unstretched total width of the at least two side panels, suitably by about 50% to about 1150%, to between about 150% and about 1250% of the unstretched total width of the at least two side panels, more suitably by about 100% to about 900%, to between about 200% and about 1000% of the unstretched total width of the at least two side panels. The total transverse stretch or elongation of the side panels 60 is roughly equal to the total transverse stretch or elongation of the stretchable outer cover 40.

Figure 5:
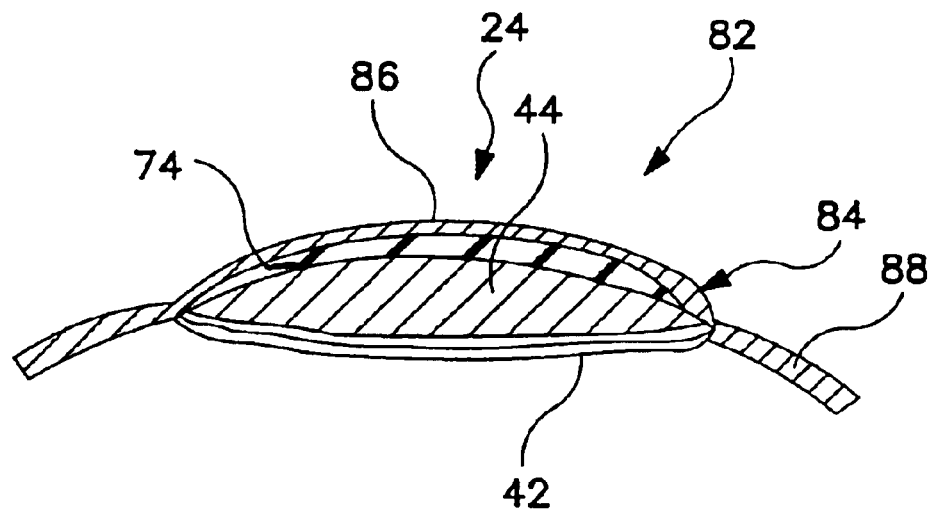
FIG. 5 is an end view of a front or back portion of an absorbent garment having a pair of stretchable side panels in a relaxed position.
Figure 6:
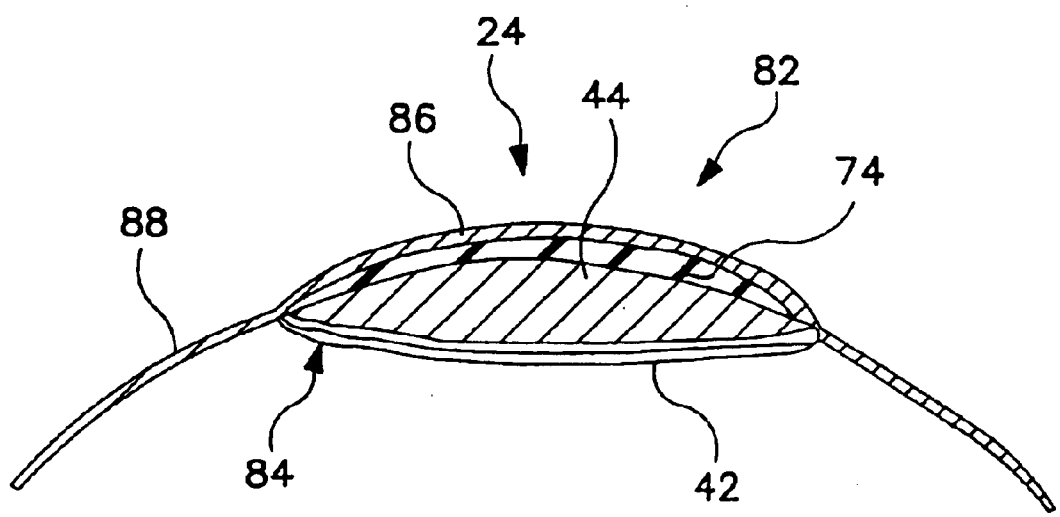
FIG. 6 is an end view of a front or back portion of an absorbent garment having a pair of stretchable side panels in a stretched position.

FIG. 5 shows an end view of a back region 24 of an absorbent mu garment 82 having a non-stretchable chassis 84, including a non-stretchable outer cover 86, a non-stretchable bodyside liner 42, and a non-stretchable absorbent assembly 44 bonded to the non-stretchable outer cover at multiple attachment points 74. A pair of stretchable side panels 88 is attached to the non-stretchable chassis 84 and the garment 82 is in a relaxed state. FIG. 6 shows the absorbent garment 82 of FIG. 5 in a transversely stretched state. As can be seen in FIGS. 5 and 6, only the stretchable side panels 88 can stretch to conform to a wearer's body, resulting in the non-stretchable chassis 84 being pulled closer towards a wearer's body, but not necessarily conforming to the wearer's body.

Figure 7:
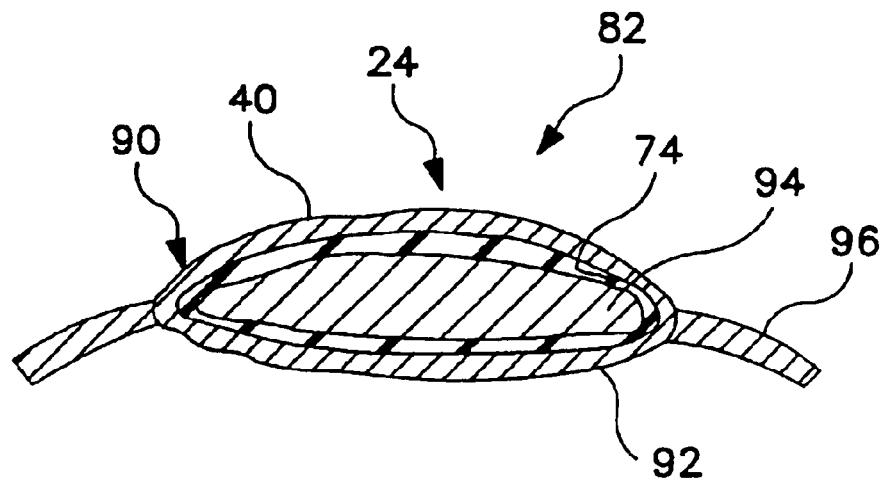
FIG. 7 is an end view of a front or back portion of an absorbent garment having a stretchable chassis in a relaxed position.
Figure 8:
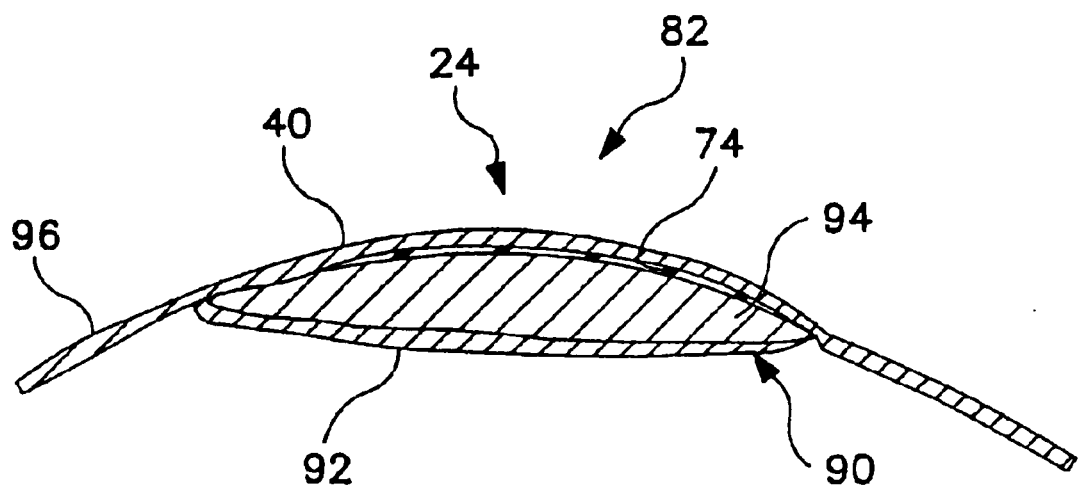
FIG. 8 is an end view of a front or back portion of an absorbent garment having a stretchable chassis in a stretched position.

FIG. 7 shows an end view of a back region 24 of an absorbent garment 82 having a completely stretchable chassis 90, including a stretchable outer cover 40, a stretchable bodyside liner 92, and a stretchable absorbent assembly 94 bonded to the stretchable outer cover at multiple attachment points 74. A pair of side panels 96, either stretchable or non-stretchable, is attached to the stretchable chassis 90 and the garment 82 is in a relaxed state. FIG. 8 shows the absorbent garment 82 of FIG. 7 in a transversely stretched state. As can be seen in FIGS. 7 and 8, the stretchable chassis 90 can stretch to conform to a wearer's body. However, difficulty remains in finding a stretchable absorbent assembly 94 and a stretchable bodyside liner 92 that have sufficient retractive forces to prevent the absorbent assembly and the bodyside liner from elongating too far and causing bagging and wrinkling of the absorbent assembly and the bodyside liner.

Figure 9:
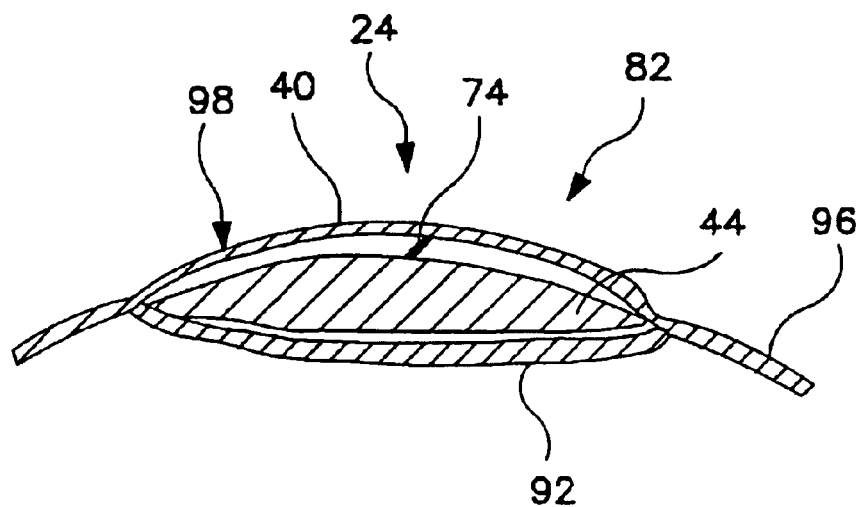
FIG. 9 is an end view of a front or back portion of an absorbent garment having a stretchable chassis in a relaxed position.
Figure 10:
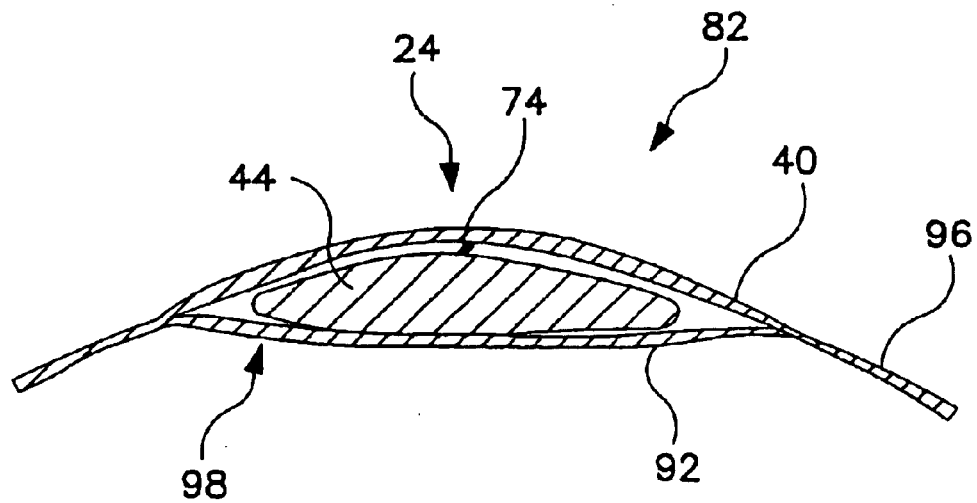
FIG. 10 is an end view of a front or back portion of an absorbent garment having a stretchable chassis in a stretched position.

FIG. 9 shows an end view of a back region 24 of an absorbent garment 82 having a stretchable chassis 98, including a stretchable outer cover 40, a stretchable bodyside liner 92, and a "free-floating" non-stretchable absorbent assembly 44 bonded to the stretchable outer cover at only one attachment point 74. A pair of side panels 96, either stretchable or non-stretchable, is attached to the stretchable chassis 98 and the garment 82 is in a relaxed state. FIG. 10 shows the absorbent garment 82 of FIG. 9 in a transversely stretched state. As can be seen in FIGS. 9 and 10, the stretchable chassis 98 can stretch to conform to a wearer's body. However, difficulty still remains in finding a stretchable bodyside liner 92 that has sufficient retractive forces to prevent the bodyside liner from elongating too far and not retracting, thereby causing bagging and wrinkling of the bodyside liner.

Figure 11:
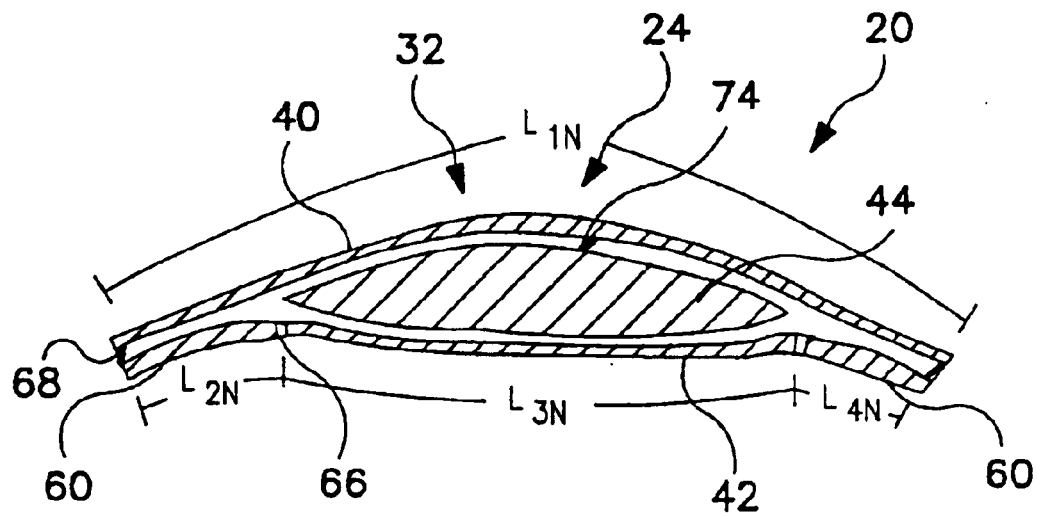
FIG. 11 is an end view of a front portion of an absorbent garment of the present invention in a relaxed position.
Figure 12:
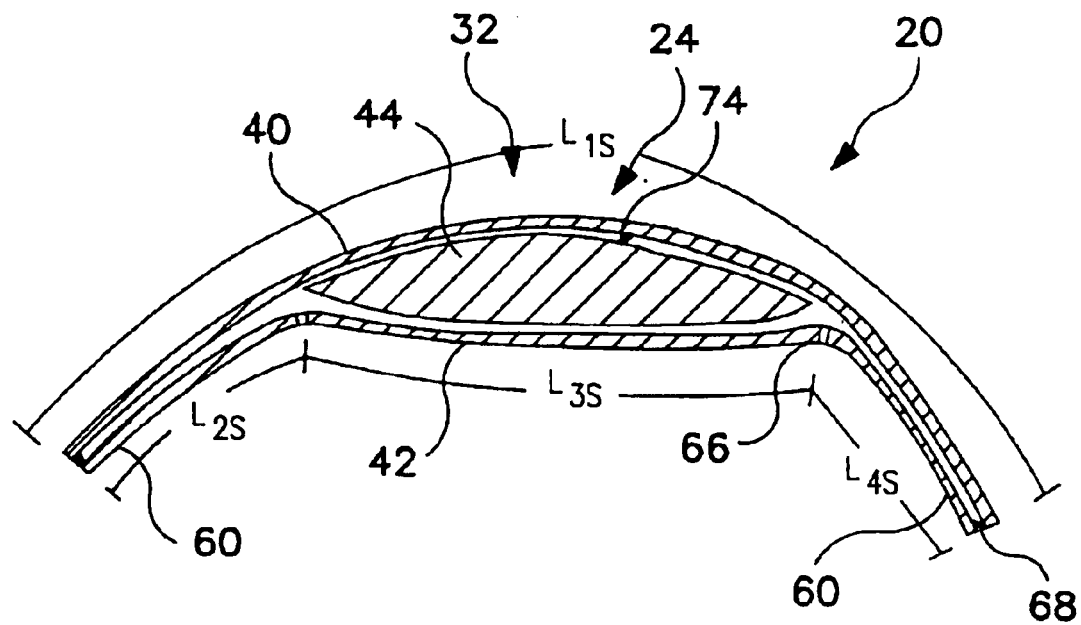
FIG. 12 is an end view of a front portion of an absorbent garment of the present invention in a stretched position.

FIG. 11 shows an end view of a back region 24 of one embodiment of the absorbent garment 20 of the present invention having a chassis 32 including the stretchable outer cover 40, the non-stretchable bodyside liner 42, and the "free-floating" non-stretchable absorbent assembly 44 bonded to the stretchable outer cover 40 at only one attachment point 74. The pair of highly stretchable side panels 60 is bonded to the non-stretchable bodyside liner 42 at attachment line 66 and to the stretchable outer cover 40 at the distal edge 68, and the garment 20 is in a relaxed state. FIG. 12 shows the absorbent garment 20 of FIG. 11 in a transversely stretched state. As can be seen in FIGS. 11 and 12, the stretchable outer cover 40 and the highly stretchable side panels 60 can stretch to conform to a wearer's body without disrupting the non-stretchable bodyside liner 42 or the non-stretchable absorbent assembly 44.

FIG. 11 identifies $L_{1N}$ as a transverse length of the stretchable outer cover 40, $L_{2N}$ and $L_{4N}$ as individual transverse lengths of the highly stretchable side panels 60, and $L_{3N}$ as a transverse length of the non-stretchable bodyside liner 42, when the absorbent garment 20 is in a non-stretched position. FIG. 12 identifies $L_{1S}$ as a transverse length of the stretchable outer cover 40, $L_{2S}$ and $L_{4S}$ as individual transverse lengths of the highly stretchable side panels 60, and $L_{3S}$ as a transverse length of the non-stretchable bodyside liner 42, when the absorbent garment 20 is in a transversely stretched position.

A percentage transverse stretch or elongation of the stretchable outer cover 40 (% stretch,) can be calculated as shown in Equation 1:

$$\%stretch_1 = 100 \times \frac{L_{1S} - L_{1N}}{L_{1N}} \quad (1)$$

Similarly, the percentages transverse stretch or elongation of the highly stretchable side panels 60 (% stretch$_2$ and % stretch$_4$) and of the non-stretchable bodyside liner 42 (% stretch$_3$) can be calculated as shown in Equations 2, 4 and 3, respectively:

$$\%stretch_2 = 100 \times \frac{L_{2S} - L_{2N}}{L_{2N}} \quad (2)$$

$$\%stretch_3 = 100 \times \frac{L_{3S} - L_{3N}}{L_{3N}} = 0 \quad (3)$$

$$\%stretch_4 = 100 \times \frac{L_{4S} - L_{4N}}{L_{4N}} \quad (4)$$

Assuming a symmetric design, the transverse lengths of the two highly stretchable side panels 60 are equal to one another ($L_{2S}=L_{4S}$ and $L_{2N}=L_{4N}$), thus the percentage transverse stretch or elongation of the two highly stretchable sides 60 are equal to one another (% stretch$_2$=% stretch$_4$). In accordance with the present invention, Equation 5 shows that the stretchable outer cover 40 can be stretched a transverse distance equal to a transverse elongation of the two highly stretchable side panels 60.

$$L_{1S}-L_{1N}=(L_{2S}-L_{2N})+(L_{4S}-L_{4N}) \quad (5)$$

Because the design is symmetric, Equation 6 holds true:

$$L_{1S}-L_{1N}=2(L_{2S}-L_{2N}) \quad (6)$$

Combining Equations 1, 2 and 6, a ratio of percentage transverse stretch of the stretchable outer cover 40 to the highly stretchable side panels 60 is calculated as shown in Equation 7:

$$\frac{\%stretch_1}{\%stretch_2} = \frac{(L_{1S}-L_{1N})/L_{1N}}{(L_{2S}-L_{2N})/L_{2N}} = 2\frac{L_{2N}}{L_{1N}} \quad (7)$$

Therefore, a minimum percentage transverse stretch of the highly stretchable side panels 60 can be determined by rearranging Equation 7 to form Equation 8:

$$\%stretch_2 = \%stretch_1 \frac{L_{1N}}{2L_{2N}} \quad (8)$$

By using a highly stretchable side panel 60 having a percentage transverse stretch equal to or greater than a value calculated in accordance with Equation 8, the stretchable outer cover 40 can stretch freely without being inhibited by the non-stretchable bodyside liner 42. For example, if the total outer cover 40 is 20 centimeters wide and is expected to stretch transversely by 50% and the side panels 60 are each 4 centimeters wide in the transverse direction 49, the side panels 60 must stretch by 125%:

$$\%stretch_2 = 50\% \frac{20 \text{ cm}}{2(4 \text{ cm})} = 125\%$$

As noted previously, the illustrated diaper 20 in FIGS. 3 and 4 has a highly stretchable front waist member 54 attached at the front waist edge 38 of the chassis 32 and a highly stretchable back waist member 56 attached at the back waist edge 39 of the chassis 32. The longitudinally opposed waist members 54 and 56 can be permanently bonded to the stretchable outer cover 40 along the waist edges 38 and 39 and to the non-stretchable bodyside liner 42 inward from the waist edges 38 and 39. By attaching the waist members 54 and 56 in this manner, the waist members 54 and 56 are each anchored to the non-stretchable bodyside liner 42 at one end, yet the waist members 54 and 56 can stretch in the longitudinal direction 48 when the outer cover 40 is stretched in the longitudinal direction. The waist members 54 and 56 may be attached using attachment means known to those skilled in the art such as adhesive, thermal or ultrasonic bonding.

In particular embodiments for improved fit and appearance, the waist members 54 and 56 of the diaper 20 desirably have an average length dimension measured parallel to the longitudinal axis 48 that is between about 3 percent and about 20 percent, and particularly between about 5 percent and about 15 percent, of the overall length dimension of the absorbent article, also measured parallel to the longitudinal axis 48. For example, in diapers having an overall length dimension of about 40 centimeters, the waist members 54 and 56 desirably have an average length dimension between about 1.2 centimeters and about 8 centimeters, such as about 4 centimeters.

Like the side panels 60 in the previous embodiment, each of the waist members 54 and 56 can include one or more individual, distinct pieces of material. The waist members 54 and 56 include an elastic material capable of stretching in a direction generally parallel to the longitudinal axis 48 of the diaper 20. Desirably, each waist member 54 and 56 is also capable of stretching in a direction generally parallel to the transverse axis 49. Materials suitable for the waist members 54 and 56 are the same materials listed as suitable for the highly stretchable side panels 60.

Like the side panels 60, the waist members 54 and 56 are highly stretchable and can be stretched by about 50% to about 1400% in the longitudinal direction, to between about 150% and about 1500% of an unstretched total width of the waist members 54 and 56, suitably by about 75% to about 1150% in the longitudinal direction, to between about 175% and about 1250% of the unstretched total width of the waist members 54 and 56, more suitably by about 100% to about 900% in the longitudinal direction, to between about 200% and about 1000% of the unstretched total width of the waist members 54 and 56. The total longitudinal stretch or elongation of the waist members 54 and 56 is roughly equal to the total longitudinal stretch or elongation of the stretchable outer cover 40.

Figure 13:
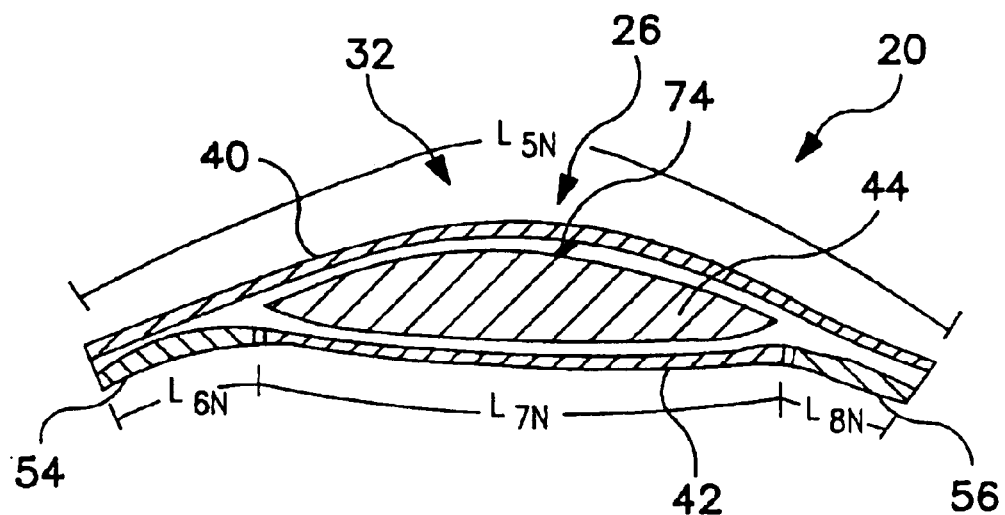
FIG. 13 is a cross-sectional side view of an absorbent garment of the present invention in a relaxed position in a longitudinal direction.
Figure 14:
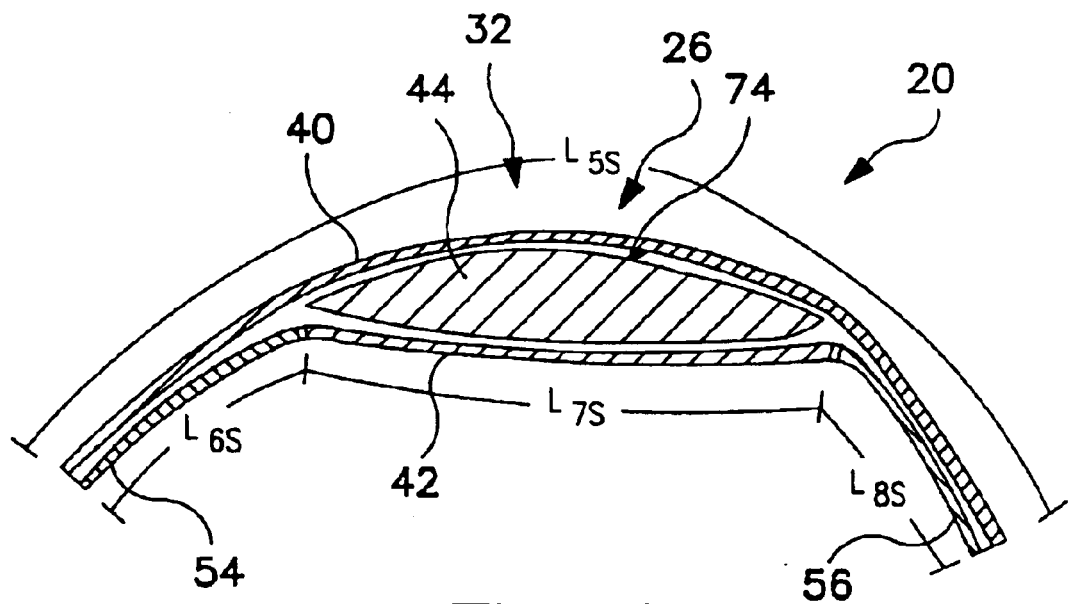
FIG. 14 is a cross-sectional side view of an absorbent garment of the present invention in a stretched position in a longitudinal direction.

FIG. 13 shows a longitudinal, cross-sectional side view of the crotch region 26 of one embodiment of the absorbent garment 20 of the pre sent invention having a chassis 32 including the stretchable outer cover 40, the non-stretchable bodyside liner 42, and the "free-floating" non-stretchable absorbent assembly 44 bonded to the stretchable outer cover 40 at only one attachment point 74. The highly stretchable front waist member 54 is bonded to the stretchable outer cover 40 at the front waist edge 38 and to the non-stretchable bodyside liner 42 inward from the front waist edge 38, and the garment 20 is in a relaxed state. FIG. 14 shows the absorbent garment 20 of FIG. 13 in a longitudinally stretched state. As can be seen in FIGS. 13 and 14, the stretchable outer cover 40 and the highly stretchable waist members 54 and 56 can stretch to conform to a wearer's body without disrupting the non-stretchable bodyside liner 42 or the non-stretchable absorbent assembly 44.

FIG. 13 identifies $L_{5N}$ as a longitudinal length of the stretchable outer cover 40, $L_{6N}$ and $L_{8N}$ as individual longitudinal lengths of the highly stretchable waist members 54 and 56, and LT as a longitudinal length of the non-stretchable bodyside liner 42, when the absorbent garment 20 is in a non-stretched position. FIG. 14 identifies $L_{5S}$ as a longitudinal length of the stretchable outer cover 40, $L_{6S}$ and $L_{8S}$ as individual longitudinal lengths of the highly stretchable waist members 54 and 56, and $L_{7S}$ as a longitudinal length of the non-stretchable bodyside liner 42, when the absorbent garment 20 is in a longitudinally stretched position.

A percentage longitudinal stretch or elongation of the stretchable outer cover 40 (% stretch$_5$) can be calculated as shown in Equation 9:

$$\%stretch_5 = 100 \times \frac{L_{5S} - L_{5N}}{L_{5N}} \qquad (9)$$

Similarly, the percentage s longitudinal stretch or elongation of the highly stretchable waist members 54 and 56 (% stretch$_6$ and % stretch$_8$) and of the non-stretchable bodyside liner 42 (% stretch$_7$) can be calculated as shown in Equations 10, 11 and 12, respectively:

$$\%stretch_6 = 100 \times \frac{L_{6S} - L_{6N}}{L_{6N}} \qquad (10)$$

$$\%stretch_7 = 100 \times \frac{L_{7S} - L_{7N}}{L_{7N}} = 0 \qquad (11)$$

$$\%stretch_8 = 100 \times \frac{L_{8S} - L_{8N}}{L_{8N}} \qquad (12)$$

Assuming a symmetric design, the longitudinal lengths of the two highly stretchable waist members 54 and 56 are equal to one another ($L_{6S}=L_{8S}$ and $L_{6N}=L_{3N}$), thus the percentage longitudinal stretch or elongation of the two highly waist members 54 and 56 are equal to one another (% stretch$_6$=% stretchs). In accordance with the present invention, Equation 13 shows that the stretchable outer cover 40 can be stretched a longitudinal distance equal to a longitudinal elongation of the two highly stretchable waist members 54 and 56.

$$L_{5S}-L_{5N}=(L_{6S}-L_{6N})+(L_{8S}-L_{8N}) \qquad (13)$$

Because the design is symmetric, Equation 14 holds true:

$$L_{5S}-L_{5N}=2(L_{6S}-L_{6N}) \qquad (14)$$

Combining Equations 9, 10 and 14, a ratio of percentage longitudinal stretch of the stretchable outer cover 40 to the highly stretchable waist members 54 and 56 is a calculated as shown in Equation 15:

$$\frac{\%stretch_5}{\%stretch_6} = \frac{(L_{5S}-L_{5N})/L_{5N}}{(L_{6S}-L_{6N})/L_{6N}} = 2\frac{L_{6N}}{L_{5N}} \qquad (15)$$

Therefore, a minimum percentage stretch of the highly stretchable waist members 54 and 56 can be determined by rearranging Equation 15 to form Equation 16:

$$\%stretch_6 = \%stretch_5 \frac{L_{5N}}{2L_{6N}} \qquad (16)$$

By using highly stretchable waist members 54 and 56 having a percentage longitudinal stretch equal to or greater than a value calculated in accordance with Equation 16, the stretchable outer cover 40 can stretch freely in the longitudinal direction 48 without being inhibited by the non-stretchable bodyside liner 42. For example, if the total outer cover 40 is 40 centimeters long and is expected to stretch by 50% and the waist members 54 and 56 are each 5 centimeters long in the longitudinal direction 48, the waist members 54 and 56 must stretch by 200%.

$$\%stretch_6 = 50\% \frac{40 \text{ cm}}{2(5 \text{ cm})} = 200\%$$

As noted previously, and shown in FIGS. 1 and 4, the diaper 20 of the present invention can have both the non-stretchable bodyside liner 42, the free-floating absorbent assembly 44, the highly stretchable side panels 60 as well as the highly stretchable waist members 54 and 56, and the stretchable outer cover 40 that stretches in both the longitudinal direction 48 and the transverse direction 49. In this embodiment, Equations 1–16, particularly 8 and 16, apply in determining the minimum percentage transverse stretch of the highly stretchable side panels 60 (% stretch$_2$) and the minimum percentage stretch of the highly stretchable waist members 54 and 56 (% stretch$_6$).

EXAMPLES

Example 1

In this example, a piece of 12.6 gsm polypropylene wettable spunbond was cut into a rectangle having a width of 5 inches and a length of 8 inches. Adhesive was applied at a 0.25 inch width around the perimeter of the rectangular piece of spunbond material. A piece of 89.1 gsm NBL, made from 0.5 osy spunbond facings necked from 130 inches to 44 inches and 20 gsm KRATON® G-2755, was cut into two pieces of material each having a width of 3 inches and a length of 8 inches, stretchable across the 3-inch width. Both NBL pieces were adhered to the spunbond, with an 8-inch length of the spunbond adhered to an 8-inch length of the NBL. A piece of 118 gsm SBL, made from 80 gsm meltblown KRATON® G-2740 and two 19 gsm polypropylene spunbond facings, was cut into two pieces of material each having a width of 3 inches and a length of 5 inches, stretchable across the 3-inch width. Both SBL pieces were adhered to the spunbond, with a 5-inch width of the spunbond adhered to a 5-inch length of the SBL. Once the NBL and SBL were adhered to the spunbond, the resulting assembly resembled a picture frame with the spunbond in the center.

Each 8-inch length of the NBL was wrapped around a wooden dowel, thereby creating a distance of 8 inches between the two pieces of doweling, 5 inches of which were the spunbond. The assembly was then stretched in the transverse direction. The distance between the doweling increased to 12 inches with easy hand pulling force. Thus, the assembly stretched 50%, from 8 inches to 12 inches. Consequently, the NBL stretched 133%, from a total of 3 inches to a total of 7 inches, since the 5-inch width of spunbond was unstretchable.

Each 5-inch length of the SBL was wrapped around a wooden dowel, thereby creating a distance of 11 inches between the two pieces of doweling, 8 inches of which were the spunbond. The assembly was then stretched longitudinally. The distance between the doweling increased to 14 inches with easy hand pulling force. Thus, the assembly stretched 27%, from 11 inches to 14 inches. Consequently, the SBL stretched 100%, from a total of 3 inches to a total of 6 inches, since the 8-inch length of spunbond was unstretchable.

The SBL separated slightly during the stretching process from the spunbond. The SBL was, therefore, removed from the spunbond, a 1-inch wide line of adhesive was applied along the 5-inch sides of the spunbond, and the SBL was reattached. Once the adhesive was set, the SBL was retested for stretching. Initial separation of the dowels was 10 inches and was readily stretched to 12.5 inches. Thus, the assembly stretched 25% while the SBL stretched 125%, from a total of 2 inches to a total of 4.5 inches, since the 8-inch length of spunbond was unstretchable.

Example 2

In this example, a HUGGIES SUPREME® STEP 4 diaper was disassembled. The absorbent layer was cut to 3.5 inch width and a 5 inch length. The outer cover was cut to a 5 inch width and an 8 inch length. A 0.25 inch wide line of adhesive was applied to the 8-inch edges of the outer cover and a 1 inch wide line of adhesive was applied to the 5-inch edges of the outer cover. The absorbent layer was then placed in the center of the spunbond assembly from Example 1 and the outer cover was then placed on top of the absorbent layer, thereby enclosing the absorbent layer between the spunbond and the outer cover to create a model diaper.

Dowels were attached to the edges of the model diaper, just as they were attached to the assembly in Example 1. Initial distance between the dowels around which the NBL was wrapped was 9 inches and readily stretched to 12 inches, for an assembly stretch of 33%. Consequently, the NBL stretched 75%, from a total of 4 inches to a total of 7 inches, since the 5-inch width of spunbond was unstretchable., Initial distance between the dowels around which the SBL was wrapped was 10.5 inches and readily stretched to 13 inches, for an assembly stretch of 24%. Consequently, the SBL stretched 100%, from a total of 2.5 inches to a total of 5 inches, since the 8-inch length of spunbond was unstretchable.

In both Example 1 and Example 2, the assembly "stretched" while the spunbond stretched a negligible amount. The absorbent assembly did not stretch at all because it was not attached to any other material but was "floating" between the spunbond and the outer cover. The capillary structure of the absorbent assembly and spunbond were not changed by the assembly stretching process.

Example 3

In this example, a central portion of a HUGGIES SUPREME® STEP 4 diaper was cut into a 5.5 inch width and a 6.25 inch length. The cut piece contained all of the normal diaper components, including a liner, a surge layer, tissue, an absorbent layer and an outer cover.

A 12-inch by 12-inch piece of commercially produced SBL with spunbond facings and a KRATON® meltblown core was obtained and the facing removed, leaving just the KRATON® meltblown. A 4-inch by 4-inch square hole was cut out of the 12-inch by 12-inch piece of meltblown. The meltblown was stretchable in all directions.

A 1-inch wide strip of adhesive was placed around the edges of the 5.5-inch by 6.25-inch mini-diaper composite. The KRATON® meltblown "picture frame" was placed on the mini-diaper and secured by the adhesive.

Two wooden dowels were wrapped in the KRATON® edges so that the dowels were aligned in the longitudinal direction of the diaper. The wrapping continued until there was a distance of 9 inches between the dowels. The doweling was easily pulled in the transverse direction to extend the KRATON® such that the dowels were 15 inches apart for a 67% assembly stretch. The KRATON® elastomer stretched 171% from an initial 3.5 inches to 9.5 inches, since the 5.5-inch width of the mini-diaper composite remained relatively unstretched.

The dowel stretching process was repeated in the longitudinal direction of the diaper. The initial distance of 9 inches was readily stretched to 13 inches for a 45% assembly stretch. The KRATON® elastomer stretched 145% from an initial 2.75 inches to 6.75 inches, since the 6.25-inch length of the mini-diaper composite remained relatively unstretched.

The dowel stretching process was repeated once again, with dowels simultaneously placed on the top and the bottom of the assembly and the assembly was then stretched simultaneously in both the longitudinal and transverse directions. The length of the assembly readily stretched from 10 inches to 14 inches for a 40% elongation at the same time that the width was readily stretched from 8 inches to 11 inches for a 37% elongation.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An absorbent garment defining a major plane surface with a transverse or X axis laying in the plane of the article and a longitudinal or Y axis laying in the plane of the article and generally perpendicular to the X axis when the garment is laid flat, comprising:
   a) a stretchable outer cover material having a major plane surface area dimension and transversely opposed side edges;
   b) an absorbent core having a major plane surface area dimension of lesser dimension than the stretchable outer cover material surface area and having a first surface and a second surface laying generally parallel to the major plane surface of the garment, the absorbent core second surface facing the stretchable outer cover material;

c) a non-stretchable bodyside liner having transversely opposed side edges and a major plane surface area dimension of lesser dimension than the stretchable outer cover material major plane surface area dimension, and a greater dimension than absorbent core major plane surface area dimension, the absorbent core first surface facing the non-stretchable bodyside liner, d) the non-stretchable bodyside liner bonded to the stretchable outer cover material so as to contain the absorbent core between the stretchable outer cover material and the non-strechable bodyside liner; and e) at least two stretchable side panels attached to the bodyside liner along the length of the transversely opposed side edges of the bodyside liner and further bonded to areas of the stretchable outer cover material outside of the non-stretchable bodyside liner; and wherein the outer cover has a percentage transverse stretch and the at least two side panels have a percentage transverse stretch equal to at least one-half the percentage transverse stretch of the outer cover times a width of the outer cover divided by a total width of the at least two side panels.

2. The absorbent garment of claim 1, wherein the outer cover can be stretched by about 50% to about 200% in a transverse direction.

3. The absorbent of claim 1, wherein the outer cover can be stretched by about 50% to about 250% in a transverse direction.

4. The absorbent garment of claim 1 wherein the stretchable side panel covers a majority of the area of the stretchable outer cover material outside of the non-stretchable bodyside liner.

5. The absorbent garment of claim 1, wherein the at least two side panel can be stretched by about 75% to about to 1400% in a transverse direction.

6. The absorbent garment of claim 1, wherein the at least two side panels can be stretched by about 50% to about 1150% in a transverse direction.

7. The absorbent garment of claim 1, wherein the at least two side panels can be stretched by about 100% to about 900% in a transverse direction.

8. The absorbent garment of claim 1, wherein the stretchable side panel covers 60% or greater of the area of the stretchable outer cover material outside of the non-stretchable bodyside liner.

9. The absorbent garment of claim 1, wherein the absorbent core is non-stretchable.

10. The absorbent garment of claim 1, wherein the outer cover forms a physical seal between the absorbent garment and a wearer at two longitudinal ends of the outer cover.

11. The absorbent garment of claim 1, wherein the outer cover comprises a stretch-bonded laminate.

12. The absorbent garment of claim 1, wherein the outer cover comprises a spunbond-meltblown-spunbond laminate.

13. The absorbent garment of claim 1, wherein the outer cover comprises a spunbonded laminate.

14. The absorbent garment of claim 1, wherein the outer cover comprises a meltblown laminate.

15. The absorbent garment of claim 1, wherein total transverse stretch of the at least two side panels is roughly equal to total transverse stretch of the outer cover.

16. The absorbent garment of claim 1, wherein the stretchable side panel covers 75% or greater of the area of the stretchable outer cover material outside of the non-stretchable bodyside liner.

17. The absorbent garment of claim 1, comprising a diaper.

18. The absorbent garment of claim 1, comprising swim wear.

19. The absorbent garment of claim 1, comprising child training pants.

20. The absorbent garment of claim 1, comprising an adult incontinence garment.

21. The absorbent garment of claim 1 wherein the stretchable side panel covers 90% or greater of the area of the stretchable outer cover material outside of the non-stretchable bodyside liner.

22. The absorbent garment according claim 1 wherein the absorbent core is free floating between the bodyside liner and the outer cover.

23. An absorbent garment defining a major plane surface with a transverse or X axis laying in the plane of the article and a longitudinal or Y axis laying in the plane of the article and generally perpendicular to the X axis when the garment is laid flat, comprising:

a) a stretchable outer cover material having a major plane surface area dimension and transversely opposed side edges;

b) an absorbent core having a major plane surface area dimension of lesser dimension than the stretchable outer cover material surface area dimension and having a first surface and a second surface laying generally parallel to the major plane surface of the garment, the absorbent core second surface facing the stretchable outer cover material;

c) a non-stretchable bodyside liner having transversely opposed side edges and a major plane surface area dimension of lesser dimension than the stretchable outer cover material major plane surface area dimension, and a greater dimension than absorbent core major plane surface area dimension, the absorbent core first surface facing the non-stretchable bodyside liner;

d) the non-stretchable bodyside liner bonded to the stretchable outer cover material so as to contain the absorbent core between the stretchable outer cover material and the non-strechable bodyside liner;

e) a first stretchable side panel attached to the bodyside liner along the length of a first transversely opposed side edge of the bodyside liner and further bonded to an area of the stretchable outer cover material outside of the surface dimensions of the non-stretchable bodyside liner; and f) a second stretchable side panel attached to the bodyside liner along the length of a second transversely opposed side edge of the bodyside liner and further bonded to an area of the stretchable outer cover material outside of the non-stretchable bodyside liner; and wherein the outer cover has a percentage transverse stretch and the first and second side panels have a percentage transverse stretch equal to at least one-half the percentage-transverse stretch of the outer cover times a width of the outer cover divided by a total width of the first and second side panels.

24. The absorbent garment of claim 23 wherein the stretchable side panel covers a majority of the area of the stretchable outer cover material outside of the non-stretchable bodyside liner.

25. The absorbent garment of claim 23 wherein the stretchable side panel covers 60% or greater of the area of the stretchable outer cover material outside of the non-stretchable bodyside liner.

26. The absorbent garment of claim 23 wherein the stretchable side panel covers 75% or greater of the area of the stretchable outer cover material outside of the non-stretchable bodyside liner.

27. The absorbent garment of claim 23 wherein the stretchable side panel covers 90% or greater of the area of the stretchable outer cover material outside of the non-stretchable bodyside liner.

28. The absorbent garment according to claim 23 wherein the absorbent core is free floating between the bodyside liner and the outer cover.

29. The absorbent garment of claim 23, wherein the outer cover can be stretched by about 50% to about 200% in a transverse direction.

30. The absorbent garment of claim 23, wherein the outer cover can be stretched by about 50% to about 250% in a transverse direction.

31. The absorbent garment of claim 23, wherein the first and second side panels can be stretched by about 75% to about 1400% in a transverse direction.

32. The absorbent garment of claim 23, wherein the first and second side panels can be stretched by about 50% to about 1150% in a transverse direction.

33. The absorbent garment of claim 23, wherein the first and second side panels can be stretched by about 100% to about 900% in a transverse direction.

34. The absorbent garment of claim 23, wherein the absorbent core is non-stretchable.

35. The absorbent garment of claim 23, wherein the outer cover forms a physical seal between the absorbent garment and a wearer at two longitudinal ends of the outer cover.

36. The absorbent garment of claim 23, wherein the outer cover comprises a stretch-bonded laminate.

37. The absorbent garment of claim 23, wherein the outer cover comprises a spunbond-meltblown-spunbond laminate.

38. The absorbent garment of claim 23, wherein the outer cover comprises a spunbonded laminate.

39. The absorbent garment of claim 23, wherein the outer cover comprises a meltblown laminate.

40. The absorbent garment of claim 23, wherein total transverse stretch of the first and second side panels is roughly equal to total transverse stretch of the outer cover.

\* \* \* \* \*

UNITED STATES PATENT AND TRADEMARK OFFICE
CERTIFICATE OF CORRECTION

PATENT NO. : 6,869,424 B1
DATED : March 22, 2005
INVENTOR(S) : Morman et al.

It is certified that error appears in the above-identified patent and that said Letters Patent is hereby corrected as shown below:

Column 21,
Line 26, insert -- garment -- after "absorbent"

Signed and Sealed this

Twelfth Day of July, 2005

JON W. DUDAS
*Director of the United States Patent and Trademark Office*